XYLENE ISOMERIZATION WITH HYDROGENATION

Original Filed June 6, 1951 2 Sheets-Sheet 1

INVENTOR
MELVIN M. HOLM
BY A. L. Snow
Frank E. Johnston
ATTORNEYS

XYLENE ISOMERIZATION WITH HYDROGENATION

Original Filed June 6, 1951 2 Sheets-Sheet 2

INVENTOR
MELVIN M. HOLM
BY A. L. Snow
Frank E. Johnston
ATTORNEYS

United States Patent Office

Re. 25,753
Reissued Apr. 6, 1965

25,753
XYLENE ISOMERIZATION WITH HYDROGENATION

Melvin M. Holm, 621 Waterview Isle, Alameda, Calif.

Original No. 2,784,241, dated Mar. 5, 1957, Ser. No. 230,168, June 6, 1951. Application for reissue July 8, 1963, Ser. No. 295,281
8 Claims. (Cl. 260—668)

Figure 1:
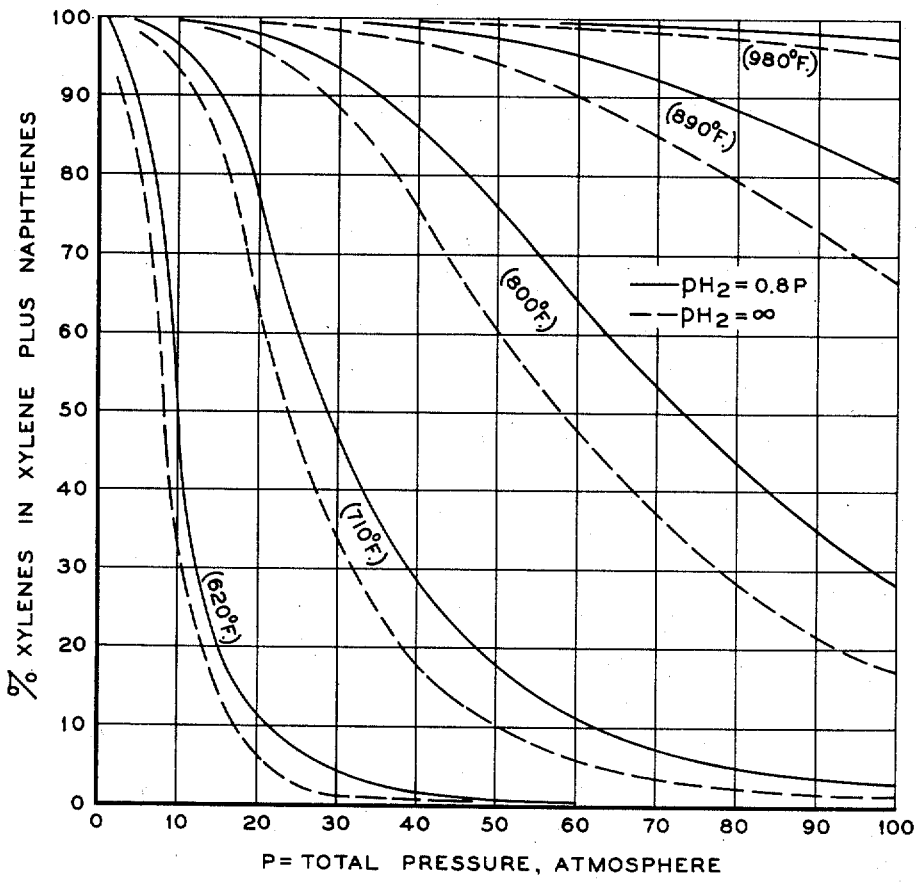

Matter enclosed in heavy brackets [ ] appears in the original patent but forms no part of this reissue specification; matter printed in italics indicates the additions made by reissue.

This invention relates to a process for isomerizing xylenes. More particularly, it relates to a process in which a single xylene isomer is converted to a substantially equilibrium mixture of the isomers or in which a non-equilibrium mixture of xylene isomers may be converted to a substantially equilibrium mixture.

Recently, efficient methods have been developed for separating individual xylene isomers from xylene mixtures and commercial uses for xylenes have been developed in which individual isomers of high purity are required. Levine Patent No. 2,474,002 describes a separation of ortho-xylene from mixed xylene isomers and the conversion of ortho-xylene to phthalic anhydride. Arnold Patent No. 2,541,682 describes an efficient method for separating para-xylene from a mixture of xylene isomers by fractional crystallization. Para-xylene, after separation, is used as a starting material in the production of terelin-type fibers. Brooke et al. Patent No. 2,521,444 describes a method for separating meta-xylene from mixed xylene isomers by extracting xylene mixtures with $HF—BF_3$.

In an equilibrium mixture of xylene isomers, the individual isomers are present in approximately the following relative amounts:

| | Percent |
|---|---|
| Ortho-xylene | 13 to 28 |
| Meta-xylene | 64 to 50 |
| Para-xylene | 23 to 22 |

One commercial method for producing mixed xylene isomers consists in hydroforming distillation fractions of naphthenic crude oils. The hydroformate is fractionally distilled to separate a $C_8$ aromatic hydrocarbon fraction which contains ethylbenzene in addition to the three xylene isomers. A mixture of $C_8$ aromatic hydrocarbons in equilibrium at 600° F. contains 5% ethylbenzene, 21% ortho-xylene, 51% meta-xylene, and 23% para-xylene. At 1000° F. the equilibrium distribution of the $C_8$ aromatic hydrocarbons is ethylbenzene 11%, ortho-xylene 23%, meta-xylene 45%, and para-xylene 21%. In a commercial undertaking in which a single xylene isomer is separated from an equilibrium mixture of isomers, a residual xylene fraction containing the undesired isomers is recovered as a raffinate, a mother-liquor, or a distillation fraction, depending upon the particular method of separation employed. This residual fraction ordinarily contains more than half of the total xylene material which is subjected to the separation process. In such an operation it would be highly desirable to isomerize the residual xylene fraction to produce further quantities of the desired isomer which could be recovered for the intended use. Numerous proposals have been made for isomerizing xylenes, but no one of the proposals heretofore made has been succesful in the sense of being sufficiently efficient to be reduced to commercial practice. At the present time no commercial xylene isomerization process is in operation.

It is an obpject of this invention to provide an efficient process for isomerizing individual xylene isomers and non-equilibrium mixtures of xylene isomers.

It has now been found that individual xylene isomers and non-equilibrium mixtures of xylene isomers may be isomerized to produce substantially equilibrium xylene mixtures by contacting the individual xylene isomer or the non-equilibrium mixture and hydrogen gas with a hydrogenation-dehydrogenation catalyst under hydrogenating conditions to convert a substantial proportion or all of the xylenes to naphthenes and then contacting the hydrogenated material and hydrogen with a hydrogenation-dehydrogenation catalyst under dehydrogenating conditions to reconvert the naphthenes to xylenes. In the course of this reconversion a substantially equilibrium mixture of xylenes is formed.

In one embodiment of the invention a two-stage process is conducted. In the first stage xylenes and hydrogen gas are contacted with a hydrogenation-dehydrogenation catalyst under hydrogenating conditions to convert a substantial proportion of the xylenes to naphthenes. In the second stage the naphthenes produced in the first stage are contacted with a hydrogenation-dehydrogenation catalyst under dehydrogenating conditions to reconvert the naphthenes to xylenes.

The terms "hydrogenating conditions," "dehydrogenation conditions" and "hydrogenation-dehydrogenation catalysts" are generally well understood in the art.

The term "hydrogenating conditions" indicates the employment of relatively low temperatures and relatively high hydrogen pressures in the operation. The temperatures employed are ordinarily below about 800° F. and usually in the range about 400 to 800° F. The hydrogen pressures employed range from a minimum level of about 20 atmospheres up to 200 atmospheres and higher. Hydrogenation occurs at the lower pressures in this range, provided that lower temperatures within the temperature range are employed, while higher pressures must be employed if higher temperatures within the temperature range are used. This relation between temperature and hydrogen pressure is well understood by those skilled in the art.

The term "dehydrogenating conditions" is generally understood to include relatively high temperatures and relatively low hydrogen pressures in the operation. Temperatures above 800° F. and up to 1200° F. may be employed and hydrogen pressures are ordinarily below about 25 atmospheres. The use of hydrogen pressure in a dehydrogenation operation serves the purpose of reducing the rate at which coke is deposited on the catalyst. When relatively high temperatures are employed in the dehydrogenation process, for example, temperatures at about 1000° F., it is possible to employ fairly high pressures of hydrogen in the process for the purpose of prolonging catalyst life. This type of operation has come into commercial practice and is generally described as catalytic reforming or hydroforming.

Hydrogenation-dehydrogenation catalysts broadly include the metals and the oxides and sulfides of the metals of groups V, VI and VIII of the periodic table. These materials are generally disposed on a suitable support, usually clay, alumina, silica alumina, and the like. Chromia-alumina, molybdena-alumina, tungsten-nickel sulfide and platinum on alumina or silica-alumina are especially effective catalysts of this character.

In another embodiment of the invention xylene vapor and hydrogen are passed through a bed of a hydrogenation-dehydrogenation catalyst. A partial pressure of hydrogen in excess of about 20 atmospheres and below about 100 atmospheres is maintained in the catalyst bed and a temperature gradient is maintained in the catalyst bed ranging from a lower temperature, usually from 600 to 800° F. in the portion of the bed adjacent to the inlet for xylenes and hydrogen, to substantially higher temperature usually in the range 800 to 1000° F. in the portion of the catalyst bed adjacent to the product outlet. In this mode of operation the conditions in the portion of the bed adjacent to the inlet are hydrogenating conditions and the conditions in the portion of the cataylst bed adjacent to the product outlet are dehydrogenating conditions. The xylenes in passing through the catalyst bed in which a gradient temperature of this character is maintained are first hydrogenated to naphthenes in the low temperature portion of the bed and then dehydrogenated to produce an equilibrium mixture of xylenes in the high temperature portion of the bed.

In another embodiment of the invention xylenes and hydrogen are contacted with a hydrogenation-dehydrogenation catalyst under conditions adapted to produce an equilibrium mixture of xylenes and naphthenes in which the naphthene content is from 10 to 30 mole percent. The conditions are so selected that the initial reaction is hydrogenation of xylenes to produce naphthene. As the naphthene content of the mixture rises, naphthene dehydrogenation begins to occur and a dynamic equilibrium in which xylenes are being hydrogenated to naphthenes and naphthenes are being dehydrogenated to xylenes is established. In this mode of operation the cataylst is maintained at a temperature in the range of 700 to 900° F. and the partial pressure of hydrogen is varied with the temperature to achieve the desired equilibrium condition from a value of 12 to 18 atmospheres at 700° F. to 60 to 96 atmospheres at 900° F. The space velocity employed in this operation is in the range 0.1 to 3.0.

Since the hydroforming of straight-run naphthenic distillates of crude oils produces a substantially equilibrium mixture of xylene isomers, it was thought that recycle of a residual xylene fraction to the hydroforming unit after the separation of an individual isomer might effect isomerization of the residual fraction to produce an equilibrium mixture. Attempts to isomerize xylenes or increase the production of a desired isomer in this manner were unsuccessful as shown in the data in the following Table I. In the runs of Table I the coprecipitated molybdena-alumina catalyst described in Claussen Patent No. 2,432,286 and now used in practically all commercial hydroforming operations was employed. Run 1315 is a normal hydroforming operation in which a straight-run naphthenic distillate boiling from 180 to 325° F. is charged to the operation. In run 1374 the feed is the mother-liquor recovered after crystalization of para-xylene from a xylene-rich fraction separated from catalytically reformed naphtha which contained about 17% para-xylene, 47% meta-xylene, 10% ortho-xylene, 12% paraffins and 12% ethylbenzene. The conditions in this run were essentially the same as those in run 1315. In run 1375 the feed is again the mother-liquor from a para-xylene crystallization process, but contact with the catalyst is made in the presence of methane instead of hydrogen.

In the runs summarized in Table I the distribution of the aromatics is shifted generally in the direction of equilibrium with respect to the isomers present, but there is no net gain in the production of para-xylene. So far as the data including liquid product yield showed, there may have been no isomerization of xylenes, but merely a preferential destruction of ortho- and meta-xylenes by cracking or demethylation.

In the following Example 1, the isomerization of xylenes by a two-stage process in which the xylenes are hydrogenated in the first stage and the produced naphthenes are dehydrogenated in the second stage to produce an approximate equilibrium mixture of xylene isomers is illustrated.

TABLE I

Xylene isomerization and recycle in the catalytic reformer

| Run No. | 1315 | | 1374 | | 1375 | |
|---|---|---|---|---|---|---|
| Feed | St. Run [5] | | Mother-Liquor [1] ($H_2$ atm.) | | Mother-Liquor ($CH_3$ atm.) | |
| Run Conditions: [2] | | | | | | |
| Temp., ° F. (Reactor Inlet) | 955 | | 965 | | 965 | |
| Space Rate, v./v./hr | 1 | | 1 | | 1 | |
| Pressure, p.s.i.g | 200 | | 200 | | 200 | |
| Recycle aromatics in feed: | | | | | | |
| Benzene | | | | | | |
| Toulene | | | | | | |
| Ethyl Benzene | | | 16.5 | 18.4 [6] | | |
| o-xylene | | | 4.4 | 4.9 | | |
| m-xylene | | | 58.4 | 65.1 | | |
| p-xylene | | | 10.4 | 11.6 | | |
| | | | 89.7 | | | |
| Aromatics in Product: [3] | | | | | | |
| Benzene | 2.6 | | 1.7 | | 1.2 | |
| Toluene | 12.0 | | 7.0 | | 6.7 | |
| Ethyl Benzene | 2.5 | 17.1 | 14.8 | 20.2 | 14.4 | 19.7 |
| o-xylene | 3.2 | 21.9 | 6.5 | 8.8 | 6.2 | 8.5 |
| m-xylene | 6.3 | 43.2 | 42.3 | 57.1 | 42.7 | 58.6 |
| p-xylene | 2.6 | 17.8 | 10.3 | 13.9 | 9.6 | 13.2 |
| Total $C_8$ | 14.6 | | 73.9 | | 72.9 | |
| Net Aromatics Produced: [4] | | | | | | |
| Benzene | 2.6 | | | | | |
| Toluene | 12.0 | | | | | |
| Ethyl Benzene | 2.5 | 17.1 | | | | |
| o-xylene | 3.2 | 21.9 | | | | |
| m-xylene | 6.3 | 43.2 | | | | |
| p-xylene | 2.6 | 17.8 | | | | |
| Total $C_8$ | 14.6 | | | | | |
| $C_2$+ Bottoms | 14.0 | | | | | |
| All Aromatics | 43.2 | | | | | |

[1] Mother-liquor from p-xylene crystallization.
[2] Adiabatic reactor; molybdena-alumina catalyst; gas recycled at 6,000 cu. ft./bbl. of feed.
[3] Vol. percent of total feed.
[4] Vol. percent of raw feed (straight run only).
[5] 180–325° F. straight run naphtha.
[6] Blocked numbers are $C_8$ aromatic distribution.

EXAMPLE 1

A sample of pure meta-xylene was hydrogenated over Raney nickel catalyst under conditions that yeilded a single naphthene isomer that was shown by spectrometric analysis to be 99+% as 1,3-dimethyl cyclohexane. This material was then dehydrogenated over a molybdena-alumina hydroforming catalyst under the following conditions:

| | |
|---|---|
| Pressure | 200 p.s.i.g. |
| Reactor inlet temperature | 955° F. |
| Liquid space rate | 1 v./v./hr. |
| Gas recyle | 6000 cu. ft./bbl. of feed. |

The yields (vol. percent) of aromatics produced were as follows:

| | | |
|---|---|---|
| Benzene | 0.3 | |
| Toluene | 2.4 | |
| Ethyl benzene | 1.3 | |
| o-xylene | 6.4 | 18.2 |
| m-xylene | 21.6 | 61.3 |
| p-xylene | 7.2 | 20.5 |
| $C_9$+ Aromatics | 1.9 | |

The following example illustrates the embodiment of the invention in which a temperature gradient is maintained in the catalyst bed.

EXAMPLE 2

The mother-liquor recovered from a fractional crystallization process for the separation of para-xylene from a substantially equilibrium mixture of xylenes produced by catalytic reforming was isomerized by passing the xylene vapors and hydrogen gas through a bed of hydrogenation-dehydrogenation catalyst. A temperature gradient ranging from a lower temperature at the inlet end of the bed to a substantially higher temperature at the outlet end of the bed was maintained. The reaction at the inlet end of the bed was primarily hydrogenation of xylenes, while the reaction at the outlet end of the bed was primarily dehydrogenation of naphthenes to produce an equilibrium mixture of xylenes. The data for two runs under these conditions are summarized in the following Table II.

TABLE II

Isomerization of Xylene Mother-Liquor

| Run No | 4-1164 | |
|---|---|---|
| Pressure, p.s.i.g. | 800 | 800 |
| Space Rate, v./v./hr | 0.5 | 1.0 |
| $H_2$ Rate, Mole/Mole of Feed | ~33 | ~25 |
| Temperatures, ° F.: | | |
| Top block | 775 | 790 |
| Bottom block | 825 | 825 |
| Catalyst top | 797 | 785 |
| Intermediate point in catalyst bed | 850 | 835 |
| Intermediate point in catalyst bed | 900 | 900 |
| Bottom | 885 | 910 |

| | Feed | Product | | | |
|---|---|---|---|---|---|
| Liquid: | | | | | |
| Gravity, ° A.P.I. | 32.7 | 48.1 | | 44.8 | |
| Aniline Point, ° F | -------- | 31 | | 1 | |
| Fractionation: | | | | | |
| Start, 194° F | -------- | 21.7 | | 23.2 | |
| 194–248 | -------- | 23.6 | | 22.0 | |
| 248–300 | 96.4 | 50.5 | | 48.9 | |
| 300+Btms | 3.6 | 4.2 | | 5.9 | |
| Analysis of 248 to 300° Cut: | | | | | |
| Ethyl Benzene | 10.6 | 6.8 | 9.0 | 7.2 | 8.4 |
| o-xylene | 15.1 | 16.2 | 21.3 | 21.0 | 24.5 |
| m-xylene | 62.3 | 35.8 | 47.2 | 39.3 | 45.8 |
| p-xylene | 4.9 | 17.1 | 22.5 | 18.3 | 21.3 |
| | | 75.9 | | 85.8 | |

NOTES:
These runs were made in a non-isothermal, non-adiabatic unit with catalyst in 2 inch I. D. Chamber surrounded by heated bronze blocks. Catalyst depth was 10 inches.
Catalyst was 3/16" molybdena-alumina pellets having a molybdena content of 9%.

The following example illustrates the embodiment of the invention in which a non-equilibrium mixture of xylene isomers is contacted with a hydrogenation-dehydrogenation catalyst under conditions adapted to produce an equilibrium mixture of xylenes and naphthenes containing 10 to 30 mole percent of naphthenes.

EXAMPLE 3

The mother-liquor recovered from a fractional crystallization process in which para-xylene was separated from a substantially equilibrium mixture of xylenes produced by catalytic reforming was isomerized by passing the xylene vapors and hydrogen through a bed of hydrogenation-dehydrogenation catalyst under conditions of temperature and hydrogen pressure adapted to produce an equilibrium mixture of xylenes and naphthenes having a naphthene content in the range about 10% to about 30%. In run 4–1173 the coprecipitated molybdena-alumina catalyst of Claussen Patent No. 2,432,286 was employed. In runs 4–1214, 4–1215 and in run 4–1232 the catalyst was platinum on alumina. The platinum catalyst used in runs 4–1214 and 4–1215 had the following composition: 1% platinum on a pure precipitated alumina, and was prepared by impregnation with chlorplatinic acid followed by calcination at 1100° F. That used in run 4–1232 was a commercial platinum-alumina catalyst containing approximately 0.3% platinum.

Runs under these conditions are summarized in the following Table III.

FIGURE 1 of the appended drawings is a graphical representation of the distribution of xylenes and naphthenes at equilibrium under varying conditions of temperature and pressure. From the graph it will be seen that an equilibrium mixture containing from 10 to 30 mole percent of naphthenes can be produced by contacting xylene vapors and hydrogen with a hydrogenation-dehydrogenation catalyst at temperatures from 700 to 900° F. and hydrogen partial pressures ranging from approximately 12 to 18 atmospheres at 700° F. to 60 to over 100 atmospheres at 900° F. When non-equilibrium mixtures of xylene isomers are subjected to these conditions, the xylenes are isomerized to produce substantially equilibrium mixtures.

Figure 2:
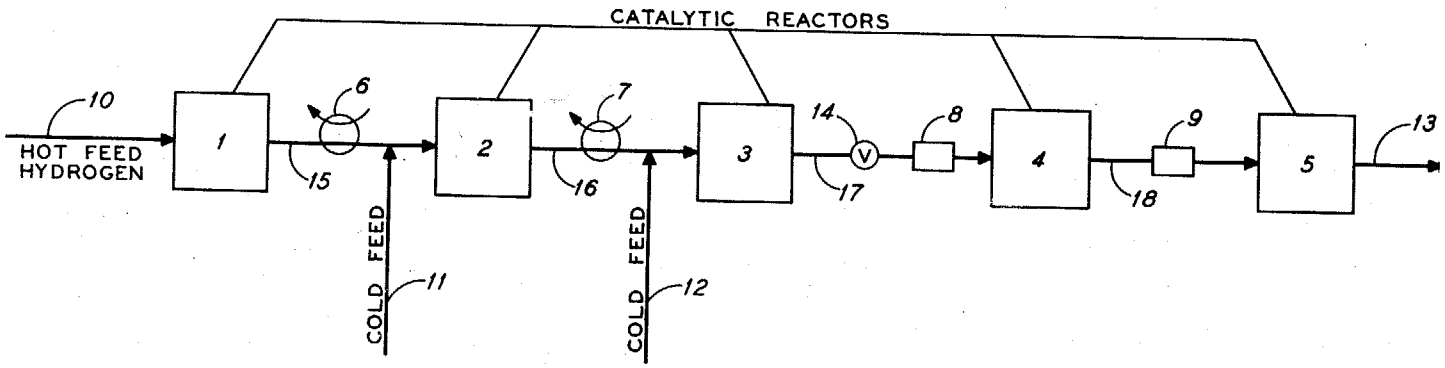

FIGURE 2 of the appended drawings diagrammatically illustrates a suitable process flow for use in isomerizing xylenes pursuant to the invention. The xylene feed and hydrogen are introduced through line 10 into catalytic reactor 1, where they contact a hydrogenation-dehydrogenation catalyst, for example, platinum on alumina. The reaction mixture produced during this contact passes through line 15 and heat exchanger 6 into catalytic reaction zone 2, where it contacts another body of the hydrogenation - dehydrogenation catalyst. The reaction product mixture produced in reactor 2 flows through line 16 and heat exchanger 7 into catalytic reaction zone 3, where it contacts still another body of the hydrogenation-dehydrogenation catalyst. Catalytic reactors 1, 2 and 3 are operated under conditions such that a substantial proportion of the xylene is hydrogenated to form naphthenes. For example, these reactors are maintained at temperatures within the range 600 to 800° F. and at a pressure about 800 p.s.i.g., the partial pressure of hydrogen in the reactors being about 500 to 600 p.s.i.g. The xylene feed is contacted with each of the three catalyst masses at space velocities in the range about 0.1 to 2.0 liquid v./v./hr. The hydrogenation reaction occurring in reactors 1, 2 and 3 is highly exothermic. Interstage cooling between the sucessive reaction zones is provided. The effluent from reaction zone 1 is cooled by passing through heat exchanger 6 and is further cooled by the introduction of cold feed and hydrogen into line 15 through line 11. Similarly, the effluent from reaction zone 2 is cooled by passing through heat exchanger 7 and further cooled by the introduction of additional cold feed and hydrogen into line 16 through line 12. The

TABLE III

Isomerization of Xylene Mother-Liquor

| Run No. | 4-1173C | | | 4-1214 | | | | 4-1215 | | 4-1232 | | |
|---|---|---|---|---|---|---|---|---|---|---|---|---|
| Pressure, p.s.i.g. | 800 | | | 800 | | | | 800 | | 500 | | |
| Space Rate, v./v./hr. | 3 | | | 1 | | | | 1 | | 2 | | |
| $H_2$ Rate, mole/mole of Feed | 15 | | | 6 | | | | 6 | | 3 | | |
| Temperatures, ° F.: | | | | | | | | | | | | |
| Top block | 900 | | | 762 | | | | 710 | | 870 | | |
| Bottom block | 900 | | | 910 | | | | 860 | | 860 | | |
| Catalyst, Top | 840 | | | 882 | | | | 853 | | 872-875 | | |
| Intermediate point in catalyst bed | 860 | | | 905 | | | | 855 | | 872-875 | | |
| Bottom | 900 | | | 935 | | | | 868 | | 872-875 | | |
| Yields: Liquid Vol. Percent | 98.5 | | | 94.1 | | | | 101.4 | | 95.5 | | |
| | Feed | | | Feed | 1st Hr. | | 2nd Hr. | | Feed | | Feed | Hrs. 1 and 2 | Hrs. 3 and 4 |
| Liquid: | | | | | | | | | | | | | |
| Gravity, ° A.P.I. | 34.0 | 35.8 | | (4-1173C.) | 46.4 | | 43.2 | | (4-1173C.) | 43.9 | 34.0 | 35.6 | 35.1 |
| Aniline Point, ° F. | | | | | 19 | | 3 | | | | 27 | −44 | −46 |
| Fractionation: | | | | | | | | | | | | | |
| Start, 194° F. | | 1.1 | | | 19.0 | | 14.7 | | | 4.0 | St. 195 0 | 4.3 | 1.8 |
| 194-248 | | 9.1 | | | 22.0 | | 21.0 | | | 27.2 | 195-240 0 | 6.1 | 5.2 |
| 248-300 | 98.4 | 87.0 | | | 53.4 | | 58.4 | | | 63.6 | 240-270 98.4% | 4.8 | 4.9 |
| 300+Bottoms | 1.6 | 2.8 | | | 5.6 | | 5.9 | | | 5.2 | 270-300 | 79.2 | 82.9 |
| | | | | | | | | | | | Btms. 1.6% | 5.6 | 5.2 |
| Analysis of 248 to 300° Cut: | | | | | | | | | | | | | |
| Ethyl Benzene | 19.7 | 14.4 | 17.1 | | 10.0 | 11.6 | 10.5 | 11.2 | | 7.3 | 10.1 | 19.7 | 15.8 | 16.4 | 14.9 | 15.7 |
| o-xylene | 7.0 | 11.5 | 13.7 | | 10.7 | 12.5 | 14.1 | 15.1 | | 12.0 | 16.7 | 7.0 | 12.8 | 13.3 | 13.4 | 14.1 |
| m-xylene | 47.8 | 43.5 | 51.7 | | 46.3 | 53.9 | 47.6 | 51.1 | | 36.6 | 50.8 | 47.8 | 51.2 | 53.0 | 49.8 | 52.7 |
| p-xylene | 11.8 | 14.7 | 17.5 | | 18.9 | 22.0 | 21.1 | 22.6 | | 16.1 | 22.4 | 11.8 | 16.7 | 17.3 | 16.6 | 17.5 |
| Total | 86.3 | 84.1 | | | 85.9 | | 93.3 | | | 72.0 | | 86.3 | 96.5 | | 94.7 | |

effluent from reaction zone 3 passes through pressure reduction valve 14 and furnace 8 into reaction zone 4, where it is contacted with an additional body of the hydrogenation-dehydrogenation catalyst. The effluent from reaction zone 4 passes through line 18 and furnace 9 into reaction zone 5, where it is contacted with still another body of the hydrogenation-dehydrogenation catalyst. The reaction product comprising isomerized xylenes is withdrawn from reaction zone 5 through line 13. Reaction zones 4 and 5 are operated under dehydrogenating conditions to convert the naphthenes formed in reaction zones 1, 2 and 3 to xylenes. Suitable conditions for employment in reaction zones 4 and 5 are temperatures in the range 950 to 1050° F., and a total pressure about 600 p.s.i.g., the partial pressure of hydrogen being in the range 300 to 400 p.s.i.g. The space velocity in reaction zones 4 and 5 is higher than that employed in reaction zones 1, 2 and 3, being from 1.2 to about 1.8 times the space velocity employed in the latter reaction zones. The dehydrogenation reaction occurring in reaction zones 4 and 5 is highly endothermic. Accordingly, the effluent from reaction zone 3 is passed through pressure reduction valve 14 to reduce the pressure by 100 to 300 p.s.i. This pressure reduction produces an increase in the temperature of the effluent from reaction zone 3. The temperature of the effluent from reaction zone 3 is further increased by passing the effluent through furnace 8 where it is heated to 950 to 1050° F. The effluent from reaction zone 4 is similarly heated by passing it through furnace 9 prior to its introduction into reaction zone 5.

The flow pattern and conditions illustrated and described with reference to FIGURE 2 may be utilized in isomerizing a single xylene isomer, or a non-equilibrium mixture of xylene isomers. Also, a mixture of xylenes and $C_8$ naphthenic hydrocarbons may be employed as the feed to the process. Up to about 50% of the total feed may be naphthenic. By using a mixture of xylenes and naphthenes, temperature control is more easily maintained in reaction zones 1, 2 and 3 and the overall process accomplishes net production of xylenes in addition to xylene isomerization.

I claim:

1. A process for recovering a desired xylene isomer from a [mixture of xylene isomers] *xylene-containing $C_8$ aromatic hydrocarbon fraction* having less than the equilibrium content of the desired isomer which comprises contacting said [xylene mixture] *hydrocarbon fraction* in vapor phase and hydrogen *in a conversion zone* with a hydrogenation-dehydrogenation catalyst *comprising platinum on a support selected from the group consisting of clay, alumina, and silica-alumina at a space velocity in the range from 0.1 to 10 v./v./hr., maintaining the conversion zone* [under conditions of temperature, pressure and hydrogen partial pressure that permit the existence of a minor amount of naphthene in equilibrium with the xylenes] *at a partial pressure of hydrogen in the range from about 20 to 100 atmospheres and at a temperature in the range from about 400 to about 800° F. in a first portion of the process and a temperature above 800° F. and up to about 1200° F. in a subsequent portion of the process, whereby hydrogenation of xylenes occurs in said first portion and formation of a substantially equilibrium mixture of xylenes occurs in said second portion,* and separating the desired xylene isomer from the *resulting* reaction product.

2. A process for recovering a desired xylene isomer from *a $C_8$ aromatic hydrocarbon fraction which contains* a mixture of xylene isomers having substantially less than the equilibrium content of the desired isomer which comprises contacting said [xylene mixture] *hydrocarbon fraction* in vapor phase and hydrogen with a hydrogenation-dehydrogenation catalyst under hydrogenating conditions *comprising a temperature in the range from 400° to 800° F. and a hydrogen pressure in the range from about 20 to 200 atmospheres* to convert a substantial proportion of the xylenes to naphthenes and then contacting the *resulting* hydrogenation reaction product with a hydrogenation-dehydrogenation catalyst *comprising platinum deposited on a support selected from the group consisting of clay, alumina and silica-alumina* under dehydrogenating conditions *comprising a temperature above about 800° and up to 1200° F., a hydrogen pressure below about 25 atmospheres and at a space velocity in the range*

*from 0.1 to 10 v./v./hr.* to convert a substantial proportion of the naphthenes to xylenes and separating the desired xylene isomer from the reaction product.

3. A process for recovering a desired xylene isomer from *a $C_8$ aromatic hydrocaron fraction which contains* a mixture of xylene isomers having substantially less than the equilibrium content of the desired isomer which comprises passing said [xylene mixture] *hydrocarbon fraction* in vapor phase *at a space velocity in the range from 0.1 to 10 v./v./hr.* and hydrogen through a bed of a hydrogenation-dehydrogenation catalyst *comprising platinum deposited on alumina,* maintaining a partial pressure of hydrogen in the range from 20 to 100 atmospheres in the catalyst bed, maintaining a temperature gradient in the catalyst bed ranging from a temperature of 600 to 800° F. in the portion of the bed adjacent the feed inlet to a substantially higher temperature in the range 800° to 1000° F. in the portion of the catalyst bed adjacent the product outlet and separating the desired xylene isomer from the effluent from the catalyst bed.

4. A process for recovering a desired xylene isomer from a mixture *consisting essentially* of xylene isomers having substantially less than the equilibrium content of the desired isomer which comprises contacting said xylene mixture in vapor phase and hydrogen with a hydrogenation-dehydrogenation catalyst *comprising* 0.3% to 1% *platinum deposited on alumina* at a temperature in the range 700° to 900° F. under a partial pressure of hydrogen ranging from 12 to 18 atmospheres at 700° F. to 60 to 100 atmospheres at 900° F. at a space velocity in the range 0.1 to 10 *v./v./hr.,* whereby a substantial proportion of the xylene is hydrogenated to naphthenes and a substantial proportion of the [remaining] xylenes *present* is isomerized and separating the desired xylene isomer from the reaction product.

5. A process for recovering a desired xylene isomer from *a $C_8$ aromatic hydrocarbon fraction containing* a mixture of xylene isomers having substantially less than the equilibrium content of the desired isomer which comprises contacting said [xylene mixture] *hydrocarbon fraction* in vapor phase and hydrogen with a hydrogenation-dehydrogenation catalyst *comprising platinum deposited on alumina* at a temperature in the range about 700° to 900° F. and under a partial pressure of hydrogen ranging from 12 to 18 atmospheres at 700° F. to 60 to 100 atmospheres at 900° F. at a space velocity in the range 0.1 to 10 v./v./hr. whereby a dynamic equilibrium mixture of xylenes and naphthenes having a naphthenic content in the range 10 to 30% by volume is produced and the individual xylene isomer distribution in the xylene portion of the mixture is substantially at equilibrium distribution, and separating the desired xylene isomer from the reaction product.

6. A process for the isomerization of xylenes which comprises contacting a mixture *consisting essentially* of xylenes in which the proportion of para-xylene is less than the equilibrium proportion *at a space velocity in the range from 0.1 to 10 v./v./hr.* with a [clay type] cracking catalyst *selected from the group consisting of clay, alumina and silica-alumina and* containing about 0.3% platinum at a temperature of about 870° F. and under a pressure of about 33 atmospheres in the presence of about 3 mols of hydrogen per mol of xylene to isomerize the xylenes.

7. A process for the isomerization of xylenes which comprises contacting a [mixture] *$C_8$ aromatic hydrocarbon fraction consisting essentially* of xylenes in which the proportion of para-xylene is less than the equilibrium proportion *at a space velocity in the range from about 0.1 to 10 v./v./hr.* with a hydrogenation-dehydrogenation catalyst *comprising platinum deposited on alumina* at a temperature in the range about 700–900° F. and under a pressure in the range about 12–96 atmospheres in the presence of about 3–25 moles of hydrogen per mole of xylene to isomerize the zylenes, the said conditions of temperature, pressure and the amount of hydrogen being correlated such that the product contains between 10% and 30% naphthenes.

8. A process for the isomerization of xylenes which comprises contacting a feed consisting essentially of a mixture of xylenes in which the proportion of para-xylene is less than the equilibrium proportion *at a space velocity in the range from about 0.1 to 10 v./v./hr.* with a [clay type] cracking catalyst *selected from the group consisting of clay, alumina and silica-alumina and* containing from about 0.3% to about 0.65% platinum at a temperature between about 700° F. and about 900° F. and under a pressure between about 12 atmospheres and about 75 atmospheres in the presence of from about 3 mols to about 6 mols of hydrogen per mol of feed to isomerize the xylenes, the said conditions of temperature, pressure and the amount of hydrogen being correlated such that the product contains between 10 and 30% naphthenes.

The following references, cited by the Examiner, are of record in the patented file of this patent or the original patent.

References Cited by the Examiner

UNITED STATES PATENTS

| | | | |
|---|---|---|---|
| 1,365,849 | 1/21 | Ramage | 260—667 |
| 2,106,735 | 3/38 | Gwynn | 260—667 |
| 2,282,231 | 5/42 | Mattox | 260—668 |
| 2,328,828 | 9/43 | Marschner | 208—56 |
| 2,356,701 | 8/44 | Ruthruff | 260—668 |
| 2,371,087 | 3/47 | Webb et al. | 260—668 |
| 2,470,712 | 5/49 | Montgomery et al. | 208—121 |
| 2,532,276 | 12/50 | Birch et al. | 260—668 |
| 2,632,779 | 3/53 | Pfennig | 260—668 |
| 2,763,623 | 9/56 | Haensel | 208—138 |

OTHER REFERENCES

Sachanen: "Chemical Constituents of Petroleum," pp. 213–15, Reinhold Pub. Co. (1945).

ALPHONSO D. SULLIVAN, *Primary Examiner.*

DANIEL E. WYMAN, *Examiner.*